United States Patent [19]
Crawford

[11] Patent Number: 5,527,526
[45] Date of Patent: Jun. 18, 1996

[54] USE OF STREPTOMYCES BACTERIA TO CONTROL PLANT PATHOGENS

[75] Inventor: Donald L. Crawford, Moscow, Id.

[73] Assignee: Idaho Research Foundation, Inc., Moscow, Id.

[21] Appl. No.: 415,353

[22] Filed: Mar. 31, 1995

Related U.S. Application Data

[63] Continuation-in-part of Ser. No. 85,448, Jun. 30, 1993, Pat. No. 5,403,584.
[51] Int. Cl.⁶ .......................... C12N 7/00; A01N 63/00; A61K 37/00; C10H 21/16
[52] U.S. Cl. ........................ 424/93.43; 435/235.5; 47/57.6
[58] Field of Search .................... 424/93 G, 93 R, 424/93.1, 93.2, 93.4, 93.43; 47/57.601, 57.605, 57.612, 57.614, 57.618, 57.6; 435/252.35, 253.5

[56] References Cited

U.S. PATENT DOCUMENTS

| | | | |
|---|---|---|---|
| 3,160,560 | 12/1964 | De Boer et al. | 435/77 |
| 4,053,627 | 10/1977 | Scher | 514/475 |
| 4,534,965 | 8/1985 | Brown et al. | 424/93.43 |
| 4,668,512 | 5/1987 | Lewis et al. | 424/93.5 |
| 5,403,584 | 4/1995 | Crawford et al. | 424/93.43 |

FOREIGN PATENT DOCUMENTS

| | | |
|---|---|---|
| 676933 | 8/1966 | Belgium. |
| 2524486 | 10/1983 | France. |
| WO93/18135 | 9/1993 | WIPO. |

OTHER PUBLICATIONS

Ames, "Mycorrhiza development in onion in response to inoculation with chitin-decomposing actinomycetes," New Phytol. 112:423–427 (1989).
Bolton, "Effects of Amending Soilless Growing Mixtures With Soil Containing Antagonistic Organisms on Root Rot and Blackleg of Geranium (*Pelargonium hortorum*) Caused by Pythium Splendens," Can. J. Plant Sci. 58:379–383 (Apr. 1978).
Bolton, "Control of *Pythium aphanidermatum* in poinsettia in a soilless culture by *Trichoderma viride* and a Streptomyces sp.," Canadian Journal of Plant Pathology 2:93–95 (1980).
Broadbent et al., "Bacteria dn Actinomycetes Antagonistic to Fungal Root Pathogens in Australian Soils," Aust. J. biol. Sci. 24:925–44 (1971).
Chambers and Millington, "Studies on *Fusarium* Species Associated with a field Planting of 'Pathogen–tested' Potatoes," Aust. J. Agric. Res. 25:293–7 (1974).
Chibata and Tosa, "Use of Immobilized Cells," Ann. Rev. Biophys. Bioeng. 10:197–216 (1981).
DeFrank and Putnam, "Screening Procedures to Identify Soil–Borne Actinomycetes That Can Produce Herbicidal Compounds," Weed Science 33:271–274 (1985).

Filonow and Lockwood, "Evaluation of Several Actinomycetes and the Fungus *Hyphochytrium catenoides* of Biocontrol Agents for Phytophthora Root Rot of Soybean," Plant Disease, vol. 69, No. 12, pp. 1033–1036 (1985).
Fravel et al., "Encapsulation of Potential Biocontrol Agents in an Alginate–Clay Matrix," Phytopathology, vol. 75, No. 7, pp. 774–777 (1985).
Hussain et al., "Biological Control of *Macrophomina phaseolina* Charcoal Rot of Sunflower and Mung Bean," J. Phytopathology 130:157–160 (1990).
Lahdenpera et al., "Mycostop—A Novel Biofungicide Based on *Streptomyces* Bacteria," published prior to 1991.
Liljeroth et al., "Assimilate Translocation to the Rhizosphere of Two Wheat Lines and Subsequent Utilization by Rhizosphere Microorganisms at Two Soil Nitrogen Concentrations," Soil Biol. Biochem., vol. 22, No. 8, pp. 1015–1021 (1990).
Lingappa and Lockwood, "Chitin Media for Selective Isolation and Culture of Actinomycetes," Phytopathology 52:317–323 (1962).
Lynch et al., "Prospects for control of *Pythium* damping–off of lettuce with *Trichoderma, Gliocladium*, and *Enterobacter* spp.," Biol Fertil Soils 11:1–5 (1991).
Merriman et al., "Effect of Bacillus and Streptomyces spp. Applied to Seed," in E. Bruehl (ed.), Biology & Control of Soil–Borne Plant Pathogens, pp. 130–133 (1977).
Meyer and Linderman, "Selective Influence on Populations of Rhizosphere or Rhizoplane Bacteria and Actinomycetes by Mycorrhizas Formed by *Glomus Fasciculatum*," Soil Biol. Biochem. vol. 18, No. 2, pp. 191–196 (1986).
Miller et al., "Variation and composition of bacterial populations in the rhizospheres of maize, wheat, and grass cultivars," Can. J. Microbiol. 35:656–660 (1989).
Miller et al., "Fluctuations in the fluorescent pseudomonad and actinomycete populations of rhizosphere and rhizoplane during the growth of spring wheat," Can. J. Microbiol. 36:254–258 (1990).
Miller et al., "The Dynamics of Actinomycetes and Fluorescent Pseudomonads in Wheat Rhizoplane and Rhizosphere," Symbiosis 9:389–391 (1990).
Mohamed, "Physiological and Antagonistic Activities of Streptomycetes in Rhizosphere of Some Plants," Egypt. J. Phytopathol. 14:121–128 (1982).
Panosyan et al., "The Nature of Physiologically Active Substances of Actinomycetes and the Effect of Their Metabolites on Plant Growth," Plant Microbe Relationships, pp. 241–245 (1965).

(List continued on next page.)

Primary Examiner—David T. Fox
Assistant Examiner—Erich E. Veitenmeimer
Attorney, Agent, or Firm—Klarquist Sparkman Campbell Leigh & Whinston

[57] ABSTRACT

This invention relates to a biocontrol formulation suitable for reducing the susceptibility of plants to fungal phytopathogens. In one aspect of the invention, a newly isolated strain of Streptomyces, Streptomyces YCED 9, is incorporated into a suitable delivery medium and applied to plant seeds or plant roots.

21 Claims, No Drawings

OTHER PUBLICATIONS

Reddi and Rao, "Antagonism of Soil Actinomycetes to Some Soil–Borne Plant Pathogenic Fungi," Indian Phytopathology, vol. 24, pp. 649–657 (1971).

Sabaou and Bounaga, "Actinomycetes parasites de champignons: etude des especes, specificite de l'action parasitaire au genre Fusarium et antagonisme dans le sol envers *Fusarium oxysporum* f.sp. *albedinis* (Killian et Maire) Gordon," Can. J. Microbiol. 33:445–451 (1987).

Scrinivasan et al., "Physiology and nutritional aspects of actinomycetes: an overview," World Journal of Microbiology and Biotechnolgy 7:171–184 (1991).

Singh and Mehrotra, "Biological Control of *Rhizoctonia bataticola* on Gram by Coating Seed with *Bacillus and Streptomyces* spp. and their Influence on Plant Growth," Plant and Soil 56:475–483 (1980).

Stevenson, "Antibiotic Activity of Actinomycetes in Soil as Demonstrated by Direct Observation Techniques," J. gen. Microbiol. 15:372–380 (1956).

Suh et al., "Production of antifungal metabolites by *Streptomyces* WYEC 108," Abstract, Society for Industrial Microbiology 49th Annual Meeting (Jul. 1992).

Sutherland and Papavizas, "Evaluation of Oospore Hyperparasites for the Control of Phytophthora Crown Rot of Pepper," J. Phytopathology 131:33–39 (1991).

Tahvonen, "Mycostop—ett biologiskt bekampningsmedel mot svampsjukdomar" (Mycostop, biological formulation for control of fungal diseases), Växtskyddsnotiser 49:5, 86–90 (1985).

Tahvonen, "Preliminary experiments into the use of *Streptomyces* spp. isolated from peat in the biological control of soil and seed–borne diseases in peat culture," Journal of the Scientific Agricultural Society of Finland 54:357–369 (1982).

Tahvonen and Avikainen, "The biological control of seed–borne *Alternaria brassicicola* of cruciferous plants with a powdery preparation of *Streptomyces* sp.," Journal of Agricultural Science in Finland 59:199–207 (1987).

Tu, "Hyperparasitism of *Streptomyces albus* on a Destructive Mycoparasite *Nectria inventa*," J. Phytopathology 117:71–76 (1986).

Turhan, "A new race of *Streptomyces ochraceiscleroticus* in the biological control of some soil–borne plant pathogens," Journal of Plant Diseases and Protection 88(7):422–434 (1981).

Turhan and Turhan, "Suppression of Damping–off on Pepper Caused by *Pythium ultimum* Trow and *Rhizoctonia solani* Kühn by Some New Antagonists in Comparison with *Trichoderma harzianum* Rifai," J. Phytopathology 126:175–182 (1989).

Walker and Connick, Jr., "Sodium Alginate for Production and Formulation of Mycoherbicides," Weed Science 31:333–338 (1983).

Williams, "Are antibiotics produced in soil?," Pedobiologia 23:427–435 (1982).

Zuberer et al., "Populations of bacteria and actinomycetes associated with sclerotia of *Phymatotrichum omnivorum* buried in Houston black clay," Plant and Soil 112:69–76 (1988).

M–L. Lahdenperä, "The Control of Fusarium Wilt on Carnation with a *Streptomyces* Preparation," Acta Horticulturae 216:85–92 (1987).

Sabaou and Bounaga, "Actinomycetes parasites de champignons: etude des especes, specificite de l'action parasitaire au genre *Fusarium* et antagonisme dans le sol envers *Fusarium oxysporum* f.sp. *albedinis* (Killian et Maire) Gordon," Can. J. Microbiol. 33:445–451 (1987).

Tahvonen, "Mycostop—ett biologiskt bekampningsmedel mot svampsjukdomar" (Mycostop, biological formulation for control of fungal diseases), Växtskyddsnotiser 49:5, 86–90 (1985).

Rothrock and Gottlieb, "Role of antibiosis in antagonism of *Streptomyces hygroscopicus* var. *geldanus* to *Rhizoctonia solani* in soil," Can. J. Microbiol. 30:1440–1447 (1984).

USE OF STREPTOMYCES BACTERIA TO CONTROL PLANT PATHOGENS

This application is a continuation-in-part of U.S. patent application Ser. No. 08/085,448 filed Jun. 30, 1993, now U.S. Pat. No. 5,403,584.

FIELD OF THE INVENTION

The present invention relates to new strains of Streptomyces bacteria that are capable of inhibiting the growth of soil borne plant pathogens and enhancing plant growth.

BACKGROUND OF THE INVENTION

Fungal phytopathogens are a cause of severe economic losses in the agricultural and horticultural industries. Many different types of fungal phytopathogens have been described: these pathogens cause plant diseases such as damping-off, white-rot, brown-rot and root-rot. Such diseases can kill emerging seedlings, reduce plant vigor and adversely affect crop yields.

To minimize fungal infections, bedding-plant nurseries may grow seedlings in steam sterilized or chemically treated soils. However, such treatments also remove beneficial microorganisms from the soil, including microorganisms that would normally compete with soil fungi. In such cases, if a fungal pathogen is accidentally introduced, it may spread rapidly and produce widespread disease.

In agricultural settings, soils infested with phytopathogenic fungi may be unsuitable for growing certain crops. For example, soybean production in Michigan and in other soybean growing states is often severely limited by Phytophthora root rot caused by the fungus *Phytophera megasperma* (Filinow and Lockwood, 1985). Species of Pythium fungi are widespread in soils in parts of California, Washington State and Idaho. *Pythium ultimum* is the most common pathogenic species encountered and is associated with pre- and post- emergence damping-off of seedlings. This species is a serious pathogen of wheat, peas and chickpeas and other crop plants grown in these soils and in soils in other states and other countries (Trapero-Casas et al., 1990; Stanghellini and Hancock, 1970; Kraft and Burke, 1971; Westerlund et al., 1988). The use of chemical agents to control fungal phytopathogens is often not practical due to high costs, lack of efficacy and the emergence of resistant strains of the fungi. Additionally, the use of chemical fungicides is not desirable from an environmental viewpoint.

It is an object of the present invention to provide new biological control means of reducing fungal pathogen infection of plants.

SUMMARY OF THE INVENTION

The foregoing object has been achieved by the isolation of a number of actinomycete bacteria that are shown to be effective in inhibiting the growth of fungal phytopathogens. In particular, two of the isolated actinomycete bacteria, herein named Streptomyces WYEC 108 and Streptomyces YCED 9, are shown to exhibit strong antagonism towards a wide range of fungal plant pathogens, including pathogens that cause the plant diseases commonly known as damping-off, root rot, white rot and brown rot. Thus, one aspect of the present invention is a biologically pure culture of Streptomyces YCED 9.

Streptomyces YCED 9 is also shown to be effective in degrading turf thatch, the grassy stem material that accumulates in turf. As a result of its ability to metabolize thatch as a carbon source, YCED 9 is well suited to growth and persistence in the rhizosphere of plants. Such growth allows optimal biocontrol activity.

The present invention sets forth various compositions suitable for treating plant seeds or plant roots with Streptomyces YCED 9. Such compositions are useful to reduce the susceptibility of plants to fungal infection, to prevent fungal infection and to reduce the accumulation of turf thatch.

In a preferred embodiment, such compositions comprise a biologically pure culture of Streptomyces YCED 9 and a delivery medium. The delivery medium serves as a support medium for the Streptomyces bacteria; it preserves the viability of the bacteria during storage and, depending on its formulation, can provide nutrients to both the Streptomyces bacteria and plants to which it is applied. In particular embodiments, the delivery medium may comprise alginate gel, peat moss, sand, cornmeal or other organic or inorganic media. In certain embodiments, a nitrogen source may be incorporated into the delivery medium. In one embodiment, the present invention encompasses a delivery medium which comprises peat moss, sand and cornmeal together with Streptomyces YCED 9. In a preferred embodiment, the delivery medium comprises at least $10^5$ colony forming units of YCED 9 per gram of delivery medium. In a more preferred embodiment, the delivery medium comprises at least $10^8$ colony forming units of YCED 9 spores per gram of delivery medium.

In another preferred formulation, the delivery medium comprises peat moss and sand and spores of YCED 9 at $10^8$–$10^9$ colony forming units per gram.

In another embodiment, the compositions comprising a biologically pure culture of Streptomyces YCED 9 and a delivery medium may be combined with supplements to enhance plant growth, such as fertilizers or other forms of plant nutrients. Other supplements to further reduce pest or disease damage may also be utilized; these include chemical pesticides and biological control agents. In one embodiment, the composition includes a biologically pure culture of Streptomyces YCED 9, a delivery medium and Streptomyces WYEC 108.

In another embodiment, the present invention encompasses alginate gel pellets containing Streptomyces YCED 9. Such pellets can be added directly to the roots of growing plants or to horticultural or agricultural soils to reduce damage to plants caused by phytopathogenic fungi.

The present invention also encompasses methods for reducing the susceptibility of a plant to fungal infection. In one embodiment, this method comprises delivering Streptomyces YCED 9 to the roots of a plant. In another embodiment, the method comprises immersing seeds in a composition that contains Streptomyces YCED 9 and thereafter planting the coated seeds in a suitable growth medium. A suitable composition for use in this method is an alginate gel containing Streptomyces YCED 9. An alternative composition for use in this method is a methyl cellulose solution containing Streptomyces YCED 9.

DETAILED DESCRIPTION OF THE INVENTION

The present invention pertains to the isolation of a number of actinomycete strains from soils. A number of these strains are shown to be effective in reducing the effects of fungal pathogens on plants, including (but not limited to) lettuce, chickpea and pepper. In particular, the present invention pertains to two Streptomyces strains herein referred to as Streptomyces WYEC 108 and Streptomyces YCED 9. These Streptomyces strains are shown to exhibit strong antagonism towards a wide range of fungal phytopathogens, including pathogens that cause pre- and post-emergence damping off of seedlings, root rot, brown rot and white rot. As such, these Streptomyces strains are particularly suitable as biocontrol agents that can be used to protect plants against infection by these phytopathogens. Thus, Streptomyces strains WYEC 108 and YCED 9 are useful in methods for reducing the susceptibility of plants to fungal infection; plants treated with these microorganisms will show reduced effects of fungal infection.

Fungal infection of susceptible untreated plants affects certain growth characteristics of such plants. For instance, untreated plants exposed to fungal pathogens may show significant reductions in plant height, plant biomass and crop yield compared to plants not exposed to the fungal pathogen. In preferred embodiments of the present of the invention, plants treated with Streptomyces WYEC 108 or Streptomyces YCED 9, or combinations of these bacteria, and subsequently exposed to the fungal pathogen will show less severe reductions in plant height, plant biomass and crop yield than untreated plants exposed to the fungal pathogen.

In more preferred embodiments, plants treated with the Streptomyces strains of the present invention and exposed to the fungal pathogen will show growth characteristics similar to the untreated, unexposed plants. In most preferred embodiments, plants treated with these strains and exposed to the fungal pathogen will show growth characteristics superior to the untreated, unexposed plants.

The Streptomyces strains of the present invention are potent antifungal biocontrol agents. These strains effectively inhibit the growth of a wide range of fungal pathogens and colonize the roots of plants in the presence of competition from rhizosphere microflora. Strain WYEC 108 enhances the growth of lettuce plants growing in steam sterilized soil and pepper plants growing in an agricultural field. Strain YCED 9 produces fungal cell wall lytic enzymes and antifungal metabolites. Strain YCED 9 is a mycoparasite of fungal hyphae and spores, and maintains a quantitatively significant presence in the rhizosphere for months. Strain YCED 9 is also shown to have the ability to degrade turf thatch. Turf thatch is the lignocellulosic material comprising dead grass stems and other vegetative matter that accumulates in turf. The ability of YCED 9 to degrade this material enhances the ability of YCED 9 to persist in the rhizosphere, where it acts to control the growth of fungal pathogens. YCED 9 may therefore be applied to turf, such as lawns or golf courses, for the dual purposes of degrading turf thatch and preventing the growth of fungal turf pathogens.

Also encompassed by this invention are means of producing vegetative cells or spores of the Streptomyces strains for incorporation into a delivery medium. The composition comprising the vegetative cells and spores of these bacteria and the delivery medium has a long shelf life and is suitable for delivering the bacteria to plants for effective control of fungal phytopathogens.

MATERIALS AND METHODS

Bacterial Growth Media

All bacterial growth media were prepared using distilled water and sterilized by autoclaving prior to use. All bacterial samples were handled using standard aseptic laboratory techniques to maintain purity.

YGM (yeast extract/glucose/mineral salts) medium: 0.6% (wt/vol) yeast extract (Difco Laboratories, Detroit, Mich.), 1.0% (wt/vol) glucose, and phosphate mineral salt solution (5.3 g of $Na_2HPO_4$, 1.98 g of $KH_2PO_4$, 0.2 g of $MgSO_4.7H_2O$, 0.2 g of NaCl, 0.05 g $CaCl_2.2H_2O$, plus 1.0 ml of trace elements (Pridham and Gottlieb, 1948) per liter of deionized $H_2O$; pH 7.1 to 7.2). The solution of trace elements consisted of 0.64 g of $CuSO_4 5H_2O$, 0.11 g of $FeSO_4.7H_2O$, 0.79 g of $MnCl_2.4H_2O$, 0.15 g of $ZnSO_4.7H_2O$ in 100 ml of distilled water.

WYE (water/yeast extract/agar) medium, modified from Reddi and Rao (1971): yeast extract (Oxoid, 0.25 g/l) as the sole carbon and nitrogen source, and agar (Oxoid, 18.0 g/l). The medium was buffered to pH 7.2–7.4 with $K_2HPO_4$ (0.5 g/l).

WYEC (water/yeast extract/cellulose/agar): WYE agar to which a thin overlay agar was added. The overlay agar contained 0.25 g/l of cellulose (Solka Floc, Sigma Chemical Co.) and 18,0 g/l agar in distilled water.

CYD (casamino acids/yeast extract/dextrose agar) medium: casamino acids (Difco: 0.5 g/l), yeast extract (Oxoid or Difco: 0.8 g/l), D-glucose (0.4 g/l), $K_2HPO_4$ (2.0 g/l; pH 7.2–7.4 ), and 18.0 g/l agar in distilled water.

YCED (casamino acids/yeast extract/dextrose/agar; modified from Reddi and Rao (1971)): yeast extract (Oxoid, 0.3 g/l) , casamino acids (Difco, 0.3 g/l), D-glucose (0.3 g/l), and agar (Oxoid, 18.0 g/l). The medium was buffered with $K_2HPO_4$ (2.0 g/l) .

CYPC (cellulose/yeast extract/peptone/compost extract/agar): cellulose (Solka Flock, Sigma Chemical Col; 5.0 g/l), yeast extract (1.0 g/l), peptone (Oxoid, 1.0 g/l), phosphate buffer ($K_2HPO_4$, 0.75 g/l), agar (18.0 g/l), and compost extract (100 ml/l) replacing 100 ml of distilled water in the medium. It was poured directly and not used as an overlay agar.

MSSC (mineral salts/starch/casein/agar; Turhan, 1981): a mineral salts solution consisting of NaCl (2.0 g/l), $MgSO_4 17H_2O$ (0.05 g/l), $CaCO_3$ (0.02 g/l), $FeSO_4 18H_2O$ (0.01 g/l), and $KNO_3$ (2.0 g/l), plus organic constituents including soluble starch (10.0 g/l) and casein (0.3 g/l), plus agar (18.0 g/l). The medium is buffered with $K_2HPO_4$ (2.0 g/l).

Sporulation agar (ATCC Medium #5): yeast extract (1.0 g/l), beef extract (1.0 g/l), tryptose (2.0 g/l), $FeSO_4$ (0.01 g/l), glucose (10.0 g/l), and agar (15.0 g/l). The medium was adjusted to pH 7.2 prior to autoclaving. (17th Edition ATCC Catalogue of Bacteria and Bacteriophages). Sporulation broth is made in the same manner except the agar is omitted.

CYG medium: Casamino acids (acid hydrolysate) (5.0 g/l), yeast extract (5.0 g/l) and glucose (10.0 g/l) in distilled water, adjusted to pH 7.1–7.2.

PDA (Potato Dextrose Agar): Potato infusion (200 g/l), dextrose (20 g/l) and agar (15 g/l). This medium is available commercially from Difco Co., Detroit, Mich. Potato Dextrose Medium (PDM) is made in the same manner except that agar is omitted.

The delivery medium, comprising sand/cornmeal/water, peat moss/sand/cornmeal or sand/peat moss in ratios as set forth below, was sterilized by steam sterilization prior to use. Sterilization was typically performed by autoclaving 3 times, each time by 90 minutes.

Harvesting of bacterial growth

For mycelial growth of Streptomyces bacteria, one liter Erlenmeyer flasks containing 500 ml YGM medium (pH 7.1–7.2) are inoculated with 20 ml of stock culture (prepared as described in Examples II and III) and incubated with shaking at 250 rpm at 30° C. for three days. Mycelia are harvested by centrifugation at 5,000 rpm for 10 minutes. Alternatively, mycelia are harvested by permitting the culture to stand until mycelia and spores settle to the bottom of the Erlenmeyer flask. Supernatant media is then decanted off and the concentrated suspension of mycelia and spores is used directly to inoculate delivery medium.

Cells and spores of Streptomyces bacteria may also be produced by growth on solid medium (for example sporulation agar or PDA). Mycelia and spores are harvested from sporulation agar or PDA by scraping the surface of the agar into distilled water. This suspension of spores and mycelia is then mixed directly into the delivery medium.

For the production of spores of Streptomyces WYEC 108 two liter Erlenmeyer flasks containing 1,200 ml YGM medium were each inoculated with 50 ml of stock culture and incubated with shaking at 250 rpm at 30° C. for 12–18 days. Spores were harvested by centrifugation at 9,000 rpm for 10 minutes. Spores of Streptomyces YCED 9 are similarly produced, except that Potato Dextrose medium or sporulation medium are preferred to YGM.

Fungal Pathogens

*Pythium ultimum* PuMXL was obtained from the culture collection of the Department of Microbiology and Crop Protection at Horticulture Research International, Worthing Road, Little Hampton, West Sussex BN17 6LP, United Kingdom. White-rot fungi *Phanerochaete chrysosporium* and *Coriolus versicolor*; brown-rot fungi *Postia placenta, Caldariomyces fumago,* and *Gloeophyllum trabeum;* soil born fungal pathogens *Rhizoctonia solani, Fusarium sambucinctum, Geotrichum candidum,* and *Verticillium dahliae* came from the culture collection of professor Don L. Crawford, Department of Bacteriology, University of Idaho, Moscow, Id. *Pythium irregulare, Phytophthora capsici, Phytophthora cinnamomi, Phytophthora parasitica, Sclerotinia cepivorum,* and *Sclerotinia sclerotiorum* came from the culture collection of Dr. Wesley Chun, Department of Plant Soil Entomology Science, University of Idaho, Moscow, Id. *Fusarium oxysporum* came from the culture collection of Dr. Arthur D. Partridge, Department of Forest Resources, University of Idaho, Moscow, Id. All cultures were maintained on potato dextrose agar or corn meal agar and grown at 25° C. These strains were identified as "pathogens" when obtained, but were not retested for their pathogenicity.

Bioassay Soil

For use in bioassays, soil naturally infested with *Pythium ultimum* was collected from several sites in the Palouse region near Moscow, Id. This soil was collected from the top 15 cm from fields that had been cropped with wheat and pea in the previous two seasons. The soil population of Pythium species was determined as follows: A soil dilution of 1.0 g air-dried soil in 50 ml sterilized distilled-water was thoroughly mixed with a Vortex tube mixer. A 0.1 ml sample of the well mixed dilution was placed as small droplets on 3-day-old 2% water agar plates (Stanghellini and Hancock, 1970). Plates were incubated at 25° C. and read periodically using a low power (×10) dissecting microscope with fluorescent illumination to determine the identity and numbers of Pythium species present. Colonies on each plate were checked after 12, 48 and 72 hours of incubation, before the final population was estimated. Identification was based upon the morphological characteristics of fungal mycelium of Pythium species under microscope and the growth pattern on 2% (w/v) water agar plates. Fungal colonies of a pure culture growing on 2% (w/v) water agar served as a control for visual identification purposes (Stanghellini and Hancock, 1970; Stasz et al., 1980).

Examination of this soil indicated that the population densities of *P. ultimum* and *P. irregulare* were 354±15 and 194±11 cfu/g of air-dried soil at the time of seeding (Spring, 1992), respectively. Population density of other Pythium species was 57±9 cfu/g of air-dried soil. *P. ultimum* and *P. irregulare* were the most prevalent species isolated from the collected soil.

EXAMPLE I

Isolation of Actinomycete Strains Exhibiting Antagonism Towards Fungal Phytopathogens Actinomycete strains were isolated from four rhizosphere-associated soil samples (samples 1, 2, 6 and 7) and four non-rhizosphere-associated soil samples (samples 3, 4, 5 and 8). These strains were then tested for utility as inhibitors of fungal phytopathogens.

Isolation of Actinomycetes

Actinomycete isolates were isolated from 8 different soils by serial-dilution/spread-plate technique. Dilutions ($10^{-5}$ to $10^{-7}$) were plated onto various agar isolation media. The composition of these media is set forth in "Materials and Methods" above. Actinomycete isolates were designated according to the isolation medium on which they were isolated. For example, WYEC 108 was isolated on WYEC medium and YCED 9 was isolated on YCED medium. In general, such media are poor in organic carbon, which effectively controls eubacterial and fungal growth and aids in isolating the slower growing actinomycetes.

Determination of pH range for growth.

Each actinomycete isolate was tested for its ability to grow at pH 5.5 to 8.0. Cultures were spot-inoculated onto plates of CYD agar, buffered to pH 5.5, 6.0, 6.5, 7.0, and 8.0 with combinations of $K_2HPO_4$ and $KH_2PO_4$ buffers at 100 mM concentration. The final pH of each medium was adjusted to its final value just prior to autoclaving. Cultures were checked for growth after 5 to 7 days incubation at 25° or 37° C. Plates were evaluated visually for little or no observable growth (±), some growth (+ or ++), or excellent growth (+++).

As shown in Table I, the rhizosphere-associated soils gave almost twice as many isolates as the non-rhizosphere-associated soils. Each isolate was tested for growth on CYD agar media ranging from pH 5.5 to pH 8.0. All isolates grew from pH to 6.5 to 8.0. Only 9 failed to grow at pH 6.0, while 57 (21%) failed to grow at pH 5.5. Of those that grew at pH 5.5, growth varied from poor to excellent depending upon the isolate. The ability of the isolates to sporulate strongly on CYD agar was also determined by visual and microscopic observation of colonies after 5–10 days of incubation.

TABLE I

| Soil | Soil pH | Selective medium YCED | WYE | Totals |
|---|---|---|---|---|
| Non-rhizosphere-associated soils | | | | 77 |
| 1 | 7.5 | 8 | 16 | 24 |
| 2 | 5.4 | 5 | 6 | 11 |
| 6 | 7.2 | 20 | 8 | 28 |
| 7 | 7.4 | 13 | 1 | 14 |
| Rhizosphere-associated soils | | | | 140 |
| 3 | 7.0 | 17 | 22 | 39 |
| 4 | 7.6 | 32 | 33 | 65 |
| 5 | 6.5 | 11 | 15 | 26 |
| 8 | 7.3 | 8 | 2 | 10 |
| Total isolates | | 114 | 103 | 217 |

In Vitro Antagonism Assay

Eighty-two isolates were chosen on the basis of their ability to grow well and sporulate strongly on CYD agar.

To test the ability of these isolates to inhibit the growth of *P. ultimum*, an in vitro plate assay was used. Each actinomycete was streak-inoculated on corn meal agar (CMA) plates, to one side of center. The culture was incubated at 25° C. for about 8 days or until the culture had sporulated. A CMA agar block (0.5 cm$^2$) containing actively growing *P. ultimum* mycelium was then aseptically placed in the center of the plate. Incubation was continued for 96 h. After 48 and 96 h the plate was examined for inhibition in the growth of *P. ultimum*. Inhibition was indicated when *P. ultimum* mycelial growth in the direction of the actinomycete colony was retarded or prevented. The results of this test are shown in Table II.

TABLE II

| Culture | Source (soil) | Growth at pH 5.5 (+ or −) | Antagonism observed[a] 48 hr | 96 hr |
|---|---|---|---|---|
| Antagonistic (at 96 hr) | | | | |
| WYEC 108 | 8 | + | +++ | +++ |
| YCED 1 | 1 | + | ++ | ++ |
| YCED 9 | 2 | + | +++ | +++ |
| YCED 35 | 4 | + | + | + |
| YCED 48 | 4 | + | + | + |
| YCED 95 | 7 | + | + | + |
| YCED 106 | 7 | + | ++ | +++ |
| WYE 21 | 4 | + | + | + |
| WYE 22 | 4 | + | + | + |
| WYE 30 | 4 | − | + | + |
| WYE 31 | 4 | + | + | + |
| WYE 78 | 1 | + | ++ | ++ |
| WYE 88 | 1 | + | + | + |
| WYE 90 | 6 | + | +++ | +++ |
| WYE 91 | 6 | + | +++ | +++ |
| WYE 97 | 1 | + | ++ | ++ |
| MSSC 1 | 2 | + | + | + |
| MSSC 2 | 2 | + | + | + |
| Nonantagonistic (at 96 hr) | | | | |
| WYE 6 | 1 | + | + | − |
| WYE 9 | 3 | + | − | − |
| WYE 11 | 3 | + | + | − |
| WYE 12 | 4 | + | + | − |
| WYE 13 | 4 | + | − | − |
| WYE 20 | 4 | + | − | − |
| WYE 23 | 3 | + | − | − |
| WYE 27 | 4 | − | − | − |
| WYE 28 | 3 | + | − | − |
| WYE 29 | 4 | + | + | ± |
| WYE 34 | 3 | + | − | − |
| WYE 35 | 3 | + | − | − |
| WYE 38 | 4 | + | − | − |
| WYE 42 | 3 | + | − | − |
| WYE 43 | 4 | + | − | − |
| WYE 45 | 3 | + | − | − |
| WYE 47 | 3 | + | − | − |
| WYE 53 | 4 | + | − | − |
| WYE 54 | 3 | + | − | − |
| WYE 56 | 3 | + | − | − |
| WYE 68 | 5 | + | − | − |
| WYE 69 | 6 | + | − | − |
| WYE 73 | 6 | + | − | − |
| WYE 75 | 2 | + | − | − |
| WYE 77 | 2 | + | ± | ± |
| WYE 84 | 2 | + | − | − |
| WYE 85 | 2 | + | − | − |
| WYE 93 | 1 | + | − | − |
| WYE 94 | 1 | + | − | − |
| WYE 120 | 8 | + | − | − |
| WYE 121 | 7 | + | − | − |
| YCED 11 | 1 | + | − | − |
| YCED 15 | 4 | + | − | − |
| YCED 16 | 4 | + | − | − |
| YCED 17 | 3 | + | − | − |
| YCED 25 | 4 | + | − | − |
| YCED 28 | 4 | + | − | − |
| YCED 29 | 3 | + | − | − |
| YCED 30 | 3 | + | − | − |
| YCED 31 | 3 | + | − | − |
| YCED 32 | 4 | + | − | − |
| YCED 41 | 4 | + | − | − |
| YCED 44 | 4 | + | ± | − |
| YCED 54 | 4 | + | − | − |
| YCED 56 | 4 | + | − | − |
| YCED 62 | 5 | + | − | − |
| YCED 64 | 5 | − | − | − |
| YCED 71 | 5 | + | − | − |
| YCED 73 | 5 | + | − | − |
| YCED 85 | 6 | − | − | − |
| YCED 88 | 5 | + | − | − |
| YCED 93 | 7 | + | − | − |
| YCED 96 | 7 | + | − | − |
| YCED 98 | 8 | + | − | − |
| YCED 105 | 7 | + | − | − |
| WYEC 101 | 4 | + | − | − |
| WYEC 104 | 8 | + | − | − |
| WYEC 107 | 7 | − | ± | − |
| WYEC 111 | 8 | + | − | − |
| WYEC 113 | 8 | + | ± | ± |
| WYEC 116 | 8 | + | − | − |
| WYEC 118 | 7 | + | − | − |
| CYPC 2 | 6 | + | − | − |
| CYPC 5 | 6 | + | − | − |

[a]Inhibition of *P. ultimum* defined as hyphal growth less abundant and growth retarded slightly on area of plate to the side where the actinomycete had been grown.
+++ very strong inhibition with zone of inhibition ≧ 2.0 cm
++ strong inhibition with zone of inhibition ≧ 1.0 cm
+ growth definitely retarded, with obvious zone of inhibition near colony
± minor inhibition of *P. ultimum* (hyphal growth less abundant and growth retarded
− no inhibition After 96 hr, five isolates (WYEC108, YCED9, YWE91, WYE90, and YCED106) showed very strong antagonism towards *P. ultimum*, four (YCED1, YCED106, WYE97, and WYE98) showed strong antagonism, and ten others showed weak antagonism. The remaining isolates were either not antagonistic, or only very weakly so. The cultures that clearly inhibited growth of *P. ultimum* were about equally divided between those isolated from rhizosphere-associated soils and non-rhizosphere-associated soils.

Seventy of the isolates that grew at pH 5.5 were also tested for their in vitro antagonism against the white-rot fungus *Phanerochaete chrysosporium* on cornmeal agar (CMA). Thirteen of the isolates showed some degree of antagonism of the white-rot fungus as shown in Table III. The degree of antagonism varied from very strong (+++) to relatively weak (+) as defined by the size of the inhibition zone. Five of the cultures that showed antagonism against *P. chrysosporium* (WYEC108, WYE78, 2YE90, YCED9, and MSSC2) were further tested on CMA against an additional white-rot fungus (*Coriolus versicolor*) and two types of brown-rot fungi (*Postia placenta* and *Gloeophyllum trabeum*). Four isolates (MSSC2, YCED9, WYE90, WYEC108) showed very strong antagonism towards the above-mentioned white- and brown- rot fungi. One isolate, WYEC78, showed strong antagonism only against the two white-rot fungi.

TABLE III

| Culture | Source (soil) | Growth at pH 5.5 (+ or −) | Antagonism observed[a] 48 hr | 96 hr |
|---|---|---|---|---|
| Antagonistic | | | | |
| WYEC 108[b] | 8 | + | +++ | +++ |
| WYE 22 | 4 | + | ++ | ++ |
| WYE 78[c] | 1 | + | + | + |
| WYE 90[b] | 6 | + | +++ | +++ |
| WYE 97 | 1 | + | ++ | ++ |
| YCED 9[b] | 2 | + | +++ | +++ |
| YCED 29 | 3 | + | + | + |
| YCED 41 | 4 | + | + | + |
| YCED 48 | 4 | + | + | + |
| YCED 95 | 7 | + | ++ | + |
| CYPC 2 | 6 | + | ++ | ++ |
| CYPC 5 | 6 | + | + | + |
| MSSC 2[b] | 2 | + | +++ | ++ |

[a]Inhibition of *P. chrysosporium* defined as hyphal growth less abundant and growth retarded slightly on area of plate to the side where the actinomycete had been grown.
+++ very strong inhibition with zone of inhibition ≧2.0 cm
++ strong inhibition with zone of inhibition ≧1.0 cm
+ growth definitely retarded, with obvious zone of inhibition near colony
± minor inhibition of *P. chrysosporium* (hyphal growth less abundant and growth retarded
− no inhibition
[b]Inhibition of *Coriolus versicolor, Postia placenta* and *Gloeophyllum trabeum* in addition to *P. chrysosporium*.
[c]Inhibition of *Postia placenta* and *Gloeophyllum trabeum* in addition to *P. chrysosporium*.

EXAMPLE II

Isolation of Streptomyces WYEC 108

Strain WYEC 108 was identified as a Streptomyces species on the basis of the morphological characteristics of the genus Streptomyces, as defined by Bergey's Manual of Systematic Bacteriology (1986). Detailed characterization of this strain is presented in U.S. patent application Ser. No. 08/085,448 which is herein incorporated by reference. Streptomyces WYEC 108 may belong to the species *Streptomyces lydicus* or a related species, as defined by Bergey's Manual of Determinative Bacteriology (1986).

EXAMPLE III

Isolation of Streptomyces YCED 9

Strain YCED 9 was identified as a Streptomyces species on the basis of the morphological characteristics of the genus Streptomyces, as defined by *Bergey's Manual of Systematic Bacteriology* (1986). YCED 9 is a filamentous bacterium that produces spiral chains of spores in an aerial mycelium. As the aerial mycelium forms, the surface of colonies on agar medium turns white. Then, as the spore chains form and mature, the aerial mycelium turns from white to gray and then to black.

As described above, Streptomyces YCED 9 was isolated as one of a number of actinomycete strains isolated from soil taken from eight different sites in Great Britain. Serial dilutions of the soil were plated out onto YCED agar and the plates were incubated at 25° C. The colonies were then picked and streaked onto YCED agar for purification. Pure colonies of YCED 9 were transferred from these plates to PDA slants, incubated at 25° C. until sporulated, and stored at 4° C. Until used. PDA is preferred for YCED 9 because the bacterium grows more rapidly and sporulates better on this medium.

Identity of Streptomyces YCED 9

As described above, the actinomycete strains isolated were examined for their ability to grow well and sporulate strongly on CYD agar. Subsequently, a number of isolates were tested for ability to inhibit the in vivo growth of the phytopathogen *Pythium ultimatum*. The isolates were also tested for in vitro antagonism against the white rot fungi *Phanerochaete chrysosporium* and *Coriolus versicolor* as well as the brown rot fungi *Postia placenta* and *Gloeophyllum trabeum*. As a result of these tests, an isolate herein referred to as Streptomyces YCED 9 was selected based on its favorable characteristics.

Various biochemical and physiological characteristics of strain YCED 9 were determined. Based on these characteristics, Streptomyces YCED 9 may belong to the species *Streptomyces violaceusiniger* (also known as *Streptomyces hygroscopicus*) or a related species, as defined by *Bergey's Manual of Determinative Bacteriology* (Volume 4, pages 2468–2492, 1989).

By way of comparison of Streptomyces YCED 9 to the type strain of *Streptomyces violaceusiniger* (ATCC 27477), the carbohydrate utilization patterns of the two strains were determined as described in *Bergey's Manual of Determinative Bacteriology* (Volume 4, pages 2468–2492, 1989). In these tests, a basal agar containing inorganic mineral salts was prepared. Filter sterilized substrates (sugars, sugar alcohols, organic acids) were added to give a final concentration of 1% (w/v) concentrations, except for the organic acids, which were at 0.1% (w/v). The results, which also include tests of two organic acids are presented in Table IV below.

TABLE IV

| Carbohydrate Tested | Growth of Strain YCED 9 | | Growth of S. hygroscopicus | |
|---|---|---|---|---|
| Basal Medium | + | (Sporulation +) | + | (Sporulation +) |
| Glucose | ++++ | (Sporulation +) | ++++ | (Sporulation +) |
| Sucrose | + | (Sporulation +) | + | (Sporulation +) |
| Galactose | +++ | (Sporulation +) | ++++ | (Sporulation +) |
| Inositol | ++ | (Sporulation +) | + | (Sporulation +) |
| Xylose | ++ | (Sporulation +) | ++ | (Sporulation +) |
| Fructose | +++ | (Sporulation +) | +++ | (Sporulation +) |
| Xylitol | ++ | (Sporulation +) | ++ | (Sporulation +) |
| Arabinose | + | (Sporulation −) | +++ | (Sporulation −) |
| Rhamnose | ++++ | (Sporulation −) | ++ | (Sporulation +) |

TABLE IV-continued

| Carbo-hydrate Tested | Growth of Strain YCED 9 | | Growth of S. hygroscopicus | |
|---|---|---|---|---|
| Lactose | +++ | (Sporulation −) | ++ | (Sporulation +) |
| Na Pyruvate | ++ | (Sporulation +) | ++ | (Sporulation +) |
| Na acetate | + | (Sporulation +) | + | (Sporulation +) |

(±) means little if any growth, while (+++) means copious growth. Intermediate levels of growth are recorded at +, ++, and +++. Basal medium value represents growth with no added carbon source.

Cultures of Streptomyces YCED 9 excrete multiple metabolites that are inhibitory to root pathogenic fungi and other microorganisms. These metabolites are produced maximally in liquid media after the culture has entered stationary phase. In flask cultures in a typical medium such as CYD broth at pH 7.0, maximal activity, as shown with biolyses or fungal inhibition on agar plates, is found after 16 days at 30° C., although significant activity is observed after 8–10 days. In contrast, cellular growth peaks after 2–3 days.

The excreted antimicrobial metabolites of Streptomyces YCED 9 are only partially inactivated by boiling and are resistant to freeze drying. The metabolites are not inactivated by protease, suggesting that they are not enzymes. Lyophilized culture supernatants containing the antimicrobial metabolites can be redissolved in water (for example at 6% w/v) but such solutions are not stable for more than a few days. However, when redissolved in ethanol at 6% w/v, the antimicrobial activity is stable at room temperature for at least 20 days.

The antimicrobial compounds produced by Streptomyces YCED 9 are extractable with organic solvents. These compounds are soluble in methanol, ethanol, n-propanol, isopropanol, and are slightly soluble in n-butanol, isobutanol, and isoamyl alcohol. Enhanced stability is observed at more basic pH levels (pH7–11) compared to acidic pH levels (<pH4). The antimicrobial compounds exhibit medium polarity on thin layer chromatography silica gel plates. The behavior of the compounds on thin layer chromatography plates using pyridine/water excludes the possibility of the compounds being primarily members of the hygromycin family. Thin layer chromatography using a methanol/chloroform solvent system shows the presence of three antimicrobial compounds. One of these compounds is associated with a strong anti-fungal activity while the other two exhibit a strong anti-bacterial activity against a Bacillus. The mobility of these compounds on thin layer chromatography suggests that they are members of the macrolide group of antibiotics and are not aminoglycosides.

ATCC Accession Number

A deposit of Streptomyces YCED 9 was made under the terms of the Budapest Treaty with the American Type Culture Collection (ATCC), Rockville, Md. on Feb. 16, 1995. This strain has been designated ATCC Accession No. 55660.

EXAMPLE IV

Preparation of Stock Cultures of Streptomyces WYEC 108 and YCED 9

For short-term use, WYEC 108 and YCED 9 are incubated on CYD agar or sporulation agar or, for YCED 9, PDA at 25° C. until sporulated and stored at 4° C. until used. For long-term storage of cultures, 10 ml spore suspensions are prepared by suspending spores from a single agar slant or plate in 10 ml of YGM for WYEC 108 and PDM for YCED 9. This spore suspension is then used to inoculate 250 ml Erlenmeyer flasks containing 100 ml YGM or PDM as appropriate. The flasks are then incubated with shaking at 250 rpm for 32–36 hours at 30° C. to provide a standard inoculum.

Samples from the standard inoculum are also used for making glycerol cultures suitable for long-term storage at −70° C. and for lyophilization. Alternatively, spores from agar plates or slants can be suspended in sterile 30% (x/v) glycerol solution and frozen at −70° C.

EXAMPLE V

In Vitro Antagonism of Fungal Phytopathogens by Streptomyces WYEC 108 and Streptomyces YCED 9

The abilities of Streptomyces YCED 9 and WYEC 108 to inhibit the growth of a wide range of fungal phytopathogens were measured in terms of colony growth inhibition. The strains were streak-inoculated to one side of the center of agar plates (corn meal agar (CMA, Difco Lab., Detroit, Mich.) for WYEC 108 and potato dextrose agar (PDA) for YCED 9). Inoculated plates were incubated at 25° C. for about 8–12 days until the cultures had sporulated. Sporulation was detectable as a mass of grey aerial mycelium and spores by observation with the naked eye and by phase contrast microscopy (×1,000).

A 5-mm-diameter CMA agar disc containing actively growing mycelium of a specific fungal phytopathogen was taken from the leading edge of a fungal culture and aseptically placed in the center of the agar plate. The plates were incubated at 25° C. until the test fungus reached the edge of a control plate not containing Streptomyces WYEC 108. Inhibition of fungal growth was quantified by determining the ratio of radial growth of fungal pathogen under the influence of Streptomyces YCED 9 or WYEC 108 versus growth alone on control plates. Percent inhibition of fungal growth was recorded after 48, 96, and 192 hr incubation depending on the selected pathogenic fungus. The bioassay was replicated on five plates, inhibition was measured separately, and recorded as an average±standard deviation.

The results of these in vitro bioassays for WYEC 108 are shown in Table V. This data shows that Streptomyces WYEC 108 exhibits very strong antagonism towards a wide range of fungal plant pathogens, including damping off (*Pythium ultimum*), root rot (*Pythium ultimum, Rhizoctonia solani, Fusarium solani,* and *Phytophthora cinnamomi*), white rot (*Phanerochaete chrysosporium* and *Coriolus versicolor*), brown rot (*Postia placenta* and *Gloeophyllum trabeum*) and leaf and stem rot (Sclerotinia sp.) fungi.

Similar results were obtained with Streptomyces YCED 9 (data not shown). YCED 9 was found to exhibit strong antifungal activity against a wide range of fungi including species of Aphanomyces (e.g., *A. euteiches*), Rhizoctonia, Phytophthora, Fusarium (e.g., *F. oxysporum, F. cinnamomi,* and *F. solani*), Pythium (e.g., *P. ultimum*), Phanerochaete (e.g., *P. chrysosporium*), and Phytomatotrichum (e.g., *P. omnivorum*). The plate assay indicated that Streptomyces YCED 9 is a stronger inhibitor of the growth of Fusarium species than is Streptomyces WYEC 108.

TABLE V

| Fungal pathogens | Percent inhibition ± standard deviation[a] Antagonism observed[b] | |
|---|---|---|
| | 48 hr | 96 hr |
| Pythium irregulare | 100 ± 0.0 | 100 ± 0.0 |
| Pythium ultimum | 100 ± 0.0 | 100 ± 0.0 |
| Rhizoctonia solani | 100 ± 0.0 | 84 ± 0.0 |
| Fusarium oxysporum | 26 ± 2.5 | 26 ± 3.6 |
| Fusarium sambucinctum | 44 ± 2.4 | 35 ± 2.4 |
| Fusarium solani | 36 ± 2.5 | 19 ± 2.5 |
| Phytophthora capsici | 100 ± 0.0 | 100 ± 0.0 |
| Phytophthora cinnamomi | 100 ± 0.0 | 100 ± 0.0 |
| Phytophthora parasitica | 100 ± 0.0 | 100 ± 0.0 |
| Sclerotinia cepivorum | 100 ± 0.0 | 95 ± 1.5 |
| Sclerotinia sclerotiorum | 100 ± 0.0 | 100 ± 0.0 |
| Phanerochaete chrysosporium | 100 ± 0.0 | 100 ± 0.0 |
| Coriolus versicolor | 100 ± 0.0 | 100 ± 0.0 |
| Postia placenta | 100 ± 0.0[c] | 100 ± 0.0[d] |
| Caldariomyces fumago | 100 ± 0.0[c] | 100 ± 0.0[d] |
| Gloeophyllum trabeum | 100 ± 0.0[c] | 100 ± 0.0[d] |
| Geotrichum candidum | 47 ± 2.1 | 45 ± 2.1 |
| Verticillium dahliae | 73 ± 2.0[c] | 59 ± 2.0[d] |

[a]Values based upon averages of individual values of five replicated plates. Individual values were determined by separately measuring the mycelial growth from each plate.
[b]Inhibition of fungal pathogens defined as hyphal growth of pathogens under the influence of Streptomyces WYEC 108 versus growth alone on the control CMA plates.
[c]and [d]% inhibition at 96 hr and 192 hr incubation, respectively.

EXAMPLE VI

Use of Streptomyces Bacteria and Their Metabolites as a Seed Treatment

Streptomyces YCED 9 and WYEC 108 bacteria may be applied to seeds to prevent subsequent fungal infection of seedlings when seeds germinate. Alternatively, seeds may be pretreated with antimicrobial metabolites of YCED 9 or WYEC 108 to achieve inhibition of fungal growth. As noted above, YCED 9 produces metabolites that are active against root pathogenic fungi and other pathogenic microorganisms.

Thus, Streptomyces YCED 9 or WYEC 108 bacteria can be used to reduce the susceptibility of plants to fungal infection by immersing plant seeds in a composition comprising Streptomyces YCED 9 or WYEC 108 and then planting the seeds in a suitable growth medium. The composition containing YCED 9 or WYEC 108 in which the seeds are immersed may be formulated as described below for WYEC 108 by suspending harvested mycelia or spores of YCED 9 or WYEC 108 in a sterilized 3% (w/v) sodium alginate solution to a density of approximately at least $10^4$ cfu/ml. After immersion in this composition, the seeds are planted in a suitable growth medium, such as nursery bedding soil or potting mix. In an alternative embodiment, 1.5% (w/v) methyl cellulose solution may be employed instead of 3% (w/v) sodium alginate solution.

Alternatively, the antimicrobial metabolites (including antifungal metabolites) produced by Streptomyces YCED 9 or WYEC 108 may be used to treat the seeds. A composition that contains the antifungal metabolites of YCED 9 or WYEC 108 can be produced as described below for WYEC 108 by growing a bacterial culture of Streptomyces YCED 9 in a suitable growth medium and then harvesting the culture supernatant from this growth medium. These antifungal metabolites may be concentrated by extraction from the culture medium using ether as described below for Streptomyces WYEC 108 metabolites, or used directly. In a preferred embodiment, the antifungal metabolites of YCED 9 or WYEC 108 are redissolved in distilled water (or in 6% w/v ethanol), filter sterilized and then added to a 3% (w/v) sodium alginate solution as described above. Seeds are then treated by immersion in this preparation and are then planted in a suitable growth medium.

By way of example, the ability of Streptomyces WYEC 108 cells to protect plants against phytopathogens was determined by applying strain WYEC 108 to ungerminated chickpea seeds and then planting these seeds in soil infested with the fungal phytopathogens P. ultimum and P. irregulare. Parallel experiments were performed using extracellular metabolites produced by WYEC 108.

Growth of Streptomyces WYEC 108

For growth of strain WYEC 108 cells, one liter Erlenmeyer flasks containing 500 ml YGM (pH 7.1–7.2) were inoculated with 20 ml of stock culture and incubated with shaking at 250 rpm at 30° C. for 3 days for the production of cell mass. For production of antifungal metabolites, one liter Erlenmeyer flasks containing 500 ml CYD (pH 7.1–7.2) were inoculated with 20 ml of stock culture and incubated with shaking at 250 rpm at 30° C. for 7 days.

Treatment of Seeds with Streptomyces WYEC 108 and Antifungal Metabolites

A mycelial suspension of Streptomyces WYEC 108 was harvested by centrifugation at. 5,000 rpm for 10 minutes from a 500 ml 3-day-old YGM liquid culture. The harvested mycelia were resuspended in 200–300 ml of sterilized 3% (w/v) sodium alginate solution to a culture density of $1.0$–$1.2 \times 10^4$ cfu/ml. Chickpea seeds were then added to the well mixed cell-alginate suspension and the seeds were transferred one by one into sterilized 0.25M $CaCl_2$ in distilled water. These seeds were used in the biocontrol assay described below.

Antifungal metabolites produced by Streptomyces WYEC 108 were obtained as follows. A 7-day-old 500 ml culture was filtered to remove cells and subsequently extracted with 150 ml ether using an extraction funnel. The ether was then removed by vacuum evaporation and the resulting extracts were redissolved in 1.5 ml distilled water. This solution was then filter sterilized through a sterile 0.45 μm filter and was added into 10 ml 3% (w/v) sodium alginate solution. The antifungal metabolite-alginate suspension was applied as described above to chickpea seeds for use in the biocontrol assay.

In Vivo Biocontrol Assay

Soil naturally infested with P. ultimum and P. irregulare is described in "Materials and Methods", above. This agricultural soil was used in this vivo biocontrol assays. Soil pH was determined to be pH 5.6 by thoroughly mixing a soil:water slurry (1:1), allowing the solids to settle for 2 h, and taking the pH of the supernatant solution. The soil was chopped, mixed thoroughly and then placed in seedling pots (10 cm deep×10 cm diameter).

The in vivo biocontrol assay was carried out by planting ungerminated chickpea seeds treated with either Streptomyces WYEC 108 or the antifungal metabolites in the infested soil. Untreated seeds planted in the same soil were used as a control. This procedure involved the following steps:

1) One cm of peat moss was placed in the bottom of each pot to prevent loss of soil while still providing for aeration and drainage.

2) Seedling pots were filled with the infested soil.

3) The soil was then watered to saturation from the bottom. After saturation of the soil surface, untreated and treated chickpea seeds were placed on the soil and covered 1.5–2.0 cm deep with the same soil. The topping was allowed to become wet by capillary action from the column of wet soil beneath. Ten seeds were planted in each of three replicate seedling pots. No fertilizer was added to the soil. To minimize drying and prevent crusting the pots were covered with clean plastic until seedling emergence. Additional water was sprayed on the top of the pots as needed, beginning after seedling emergence. Experiments were performed in a greenhouse at 15–30° C. with a 12 hr light and 12 hr dark cycle photoperiod (16,000 lux).

Emergence counts of chickpea seedlings were made periodically, and final emergence counts were taken after 20 days. Emergence data were reported as the average for each treatment. The ability of Streptomyces WYEC 108 to act as a biocontrol agent was based on total emergence, plant height, and plant fresh weight, as compared to the control plants grown from untreated seeds with the biocontrol agent. The results of this biocontrol assay are shown in Table VI.

TABLE VI

| Treatment | Damping-off (%) | | Emergence (%) | Height (cm) | Fresh weight (g/plant) |
| --- | --- | --- | --- | --- | --- |
| | Pre-emergence | Post-emergence | | | |
| Control | 86.7 | 6.6 | 6.7 | 4.3$^x$ | 0.34$^x$ |
| Streptomyces WYEC 108$^c$ | 36.7 | 0.0 | 63.3 | 11.3 | 1.05 |
| 3% Alginate$^d$ | 83.3 | 10.0 | 6.7 | 4.1$^x$ | 0.32$^x$ |
| Antifungal metabolites$^e$ | 63.3 | 3.3 | 33.3 | 8.9 | 0.66 |

$^c$In 3% alginate, coated on seeds.
$^d$Not containing WYEC 108.
$^x$Means so marked within column were not significantly different at the P = 0.05 level.

Both Streptomyces WYEC 108 cells and the antifungal metabolites produced by these cells reduced Pythium damping-off of the chickpeas.

Plants showed vigorous growth, when seeds were coated with Streptomyces WYEC 108 cells. There was a significant reduction in height and fresh weight of the plants that emerged from the control (untreated) chickpea seeds as compared to those of the plants germinated from seeds coated with Streptomyces WYEC 108 cells. Emergence of untreated chickpea seeds was extremely reduced (6.7% emergence) because of seed rot and preemergence damping-off disease caused by *P. ultimum* when seeds were planted in soil naturally infested with *P. ultimum* and *P. irregulare*. In contrast, emergence of seeds treated with Streptomyces WYEC 108 cells before seeding was 63.3%. Seeds treated with alginate alone did not show increased emergence. Symptoms typical of Pythium root rot, including root hair loss and root discoloration, were evident in harvested chickpea roots germinated from control seeds, but these symptoms were absent from plants grown from seeds treated with Streptomyces WYEC 108 cells. In the controls, damage to chickpea was mainly in the form of seed decay, and preemergence damping-off. Chickpea seedlings that did emerge and grow were stunted, and their roots were severely infected with *P. ultimum*. In a side by side comparison of chickpea plants taken from the biocontrol assay, the control plant, which was germinated from untreated seeds showed extensive root infection and lack of secondary roots and root hairs whereas the plants emerging from seeds coated with Streptomyces WYEC 108 showed good growth and normal formation of secondary roots and root hairs.

Emergence of chickpea seeds treated with antifungal metabolites in the form of ether soluble metabolite was higher (33.3%) than that of control seeds (6.7%), but lower than that of seeds coated with Streptomyces WYEC 108 cells (63.3%). Plants that emerged from seeds treated with antifungal metabolites showed vigorous growth, longer root, and a higher density of root hair development as compared to control plants.

Accordingly, one aspect of the present invention is the use of Streptomyces YCED 9 or Streptomyces WYEC 108 or the metabolites of these bacteria in the treatment of seeds.

EXAMPLE VII

Ability of Streptomyces YCED 9 to Metabolize Turf Thatch

An important characteristic of Streptomyces YCED 9 is its ability to degrade and metabolize lignocellulosic materials, such as turf thatch. Thatch is the dead material including grass stems and other vegetative matter that accumulates in turf. Thatch build up in lawns, golf courses and other cultivated turf grasses can inhibit healthy growth and promote weeds and fungal pathogens. Streptomyces YCED 9 is able to metabolize turf thatch and utilize it as a carbon source. As a result, YCED 9 is able to effectively colonize and persist in the rhizosphere. The ability of YCED 9 to persist in the rhizosphere enhances its ability to control the growth of fungal pathogens.

The ability of Streptomyces YCED 9 to metabolize turf thatch is illustrated by experiments in which spores of YCED 9 are incubated with sterile turf thatch. Essentially, 1–2 g of turf thatch is sterilized by autoclaving in a flask. The sterile flask is the inoculated with spores of Streptomyces YCED 9 in a sterile solution of phosphate buffered yeast extract (0.3% w/v, pH 6.5–7.5). Following inoculation, the flask is incubated at 30° C. Replicate flasks are harvested periodically and the amount of thatch remaining is quantified gravimetrically (i.e., the thatch is harvested, washed, dried and weighed). Typically, after three weeks of incubation, approximately 28% by weight of the turf thatch is metabolized. This rate of degradation is substantial, considering the highly lignified nature of the turf thatch and its normal recalcitrance to degradation.

EXAMPLE VIII

Incorporation of Streptomyces Bacteria into Delivery Medium

A composition suitable for the long term storage of viable Streptomyces spores and suitable for delivery of the spores to plants is formulated as described below. This method may be used directly for YCED 9. For incorporation of WYEC 108 spores, the method is preferably modified by using YGM medium in place of PDM.

One liter Erlenmeyer flasks containing 500 ml Potato Dextrose medium (PDM) are inoculated with 20 ml of stock culture (for example Streptomyces YCED 9) and incubated with shaking at 250 rpm at 30° C. for three days. After incubation, the culture is harvested by centrifugation at 5,000 rpm for 10 minutes. The harvested material is resuspended in 1600 ml of 10% PDM and mixed with sterilized 8 g NH$_4$Cl dissolved in 400 ml distilled water. The two liters of cell and NH$_4$Cl mixture are then inoculated into a plastic container containing 4 kg sterilized delivery medium consisting of a sand-water-cornmeal mixture in a 9-2-1 (w/w) ratio. The delivery medium is sterilized twice (3 hr at 121° C.) before incubation of the culture. This mixture is incubated for 10–14 days at 25° C. to maximize the number of spores present in the mixture prior to storage at 4° C. until use. The bacteria produce spores during the 10–14 days incubation resulting in increased cfu/g of delivery medium.

. Alternatively instead of YGM or PDM media, cells and spores can be produced in CYG medium. As an alternative to harvesting cells by centrifugation, culture flasks may also be allowed to stand so that the bacterial mycelia and spores settle. Thereafter, the clear supernatant is decanted and the concentrated mycelia/spore suspension is inoculated directly into the delivery medium. When this harvesting procedure is utilized, it is not necessary to add NH$_4$Cl to the medium since the bacterial growth medium is a suitable source of nitrogen.

A preferred formulation for the field use of Streptomyces YCED 9 is the incorporation of YCED 9 spores into a delivery medium consisting of peat moss and sand. Preferably, YCED 9 spores are added to the delivery medium to produce a final concentration of $10^8$–$10^9$ colony forming units per gram of delivery medium. A typical unit of this formulation is produced in the following manner: spores from 50–100 sporulated PDA plates of Streptomyces YCED 9 are aseptically scraped off the surface of the plates and added to 90 grams of sterile sand. This sand is then mixed into a mixture of sterile sand/peat moss (in a ratio of 1600 grams of sand to 310 grams of peat moss). This formulation can then be stored at room temperature or in the refrigerators for 6–8 months. Storage for this length of time typically result in less than one log reduction in the viability of the spores. Although the ratio of sand to peat moss may readily be varied, by up to at least 25%, the ratio given above is the preferred ratio.

EXAMPLE IX

Use of Streptomyces WYEC 108 in Delivery Medium in the Field

In vivo biocontrol assays were carried out to determine the effectiveness of Streptomyces WYEC 108 as a biocontrol agent when incorporated into the delivery medium described above.

Streptomyces WYEC 108 was produced and incorporated into the delivery medium as described in Example VII above, using Streptomyces WYEC 108 grown for three days in YGM medium. The initial population of Streptomyces WYEC 108 in the delivery medium was determined to be approximately $1.0$–$1.2 \times 10^5$ cfr/g of soil by plate counts on CYD plates immediately prior to planting seedlings in the pots. This treated soil was then used to fill seedling pots (4 cm by 13.5 cm).

Control plants were grown in pots containing steam sterilized soil (sterilized at 100° C. for 60 minutes).

Pepper seedlings (green, hot peppers) were then planted in the seedling pots containing either steam sterilized soil only or a mixture of steam sterilized soil inoculated with the delivery medium containing Streptomyces WYEC 108. After six weeks of growth in a greenhouse, these plants were transplanted to an agricultural field. In some instances, 100 g of the delivery medium containing 450±17 cfu/g of *Phytophthora parasitica* was inoculated into the planting hole prior to transplantation.

Plant height was determined 55 days after transplantation and recorded as a mean value. Plant biomass was determined by harvesting and measuring fresh weight of the plants after 110 days of cultivation post transplantation. At that time, the number of peppers formed and the weight of peppers per plant were recorded as a mean value. The results of this field trial are shown in Table VII.

TABLE VII

| Treatment | Plant Height (cm) | Biomass fresh weight (g/plant) | # of pepper per plant | Yield of pepper fresh weight (g/plant) |
|---|---|---|---|---|
| [b]Control: | | | | |
| Untreated | 22.4k[y] | 274.1k[y] | 19.1k[y] | 158.8k[y] |
| [c]Treated with WYEC 108 | 29.1m | 353.3m | 36.5m | 279.8m |
| [b]Untreated + P. parasitica[d] | 20.3k | 238.5k | 13.8k | 151.2k |
| [c]Treated with WYEC 108 + P. parasitica[d] | 28.6m | 266.6k | 22.7k | 221.6k |

[b]Pepper plants grown in pots (4 cm × 13.5 cm) containing steam sterilized soil only.
[c]Pepper plants grown in pots containing a mixture of steam sterilized soil and delivery medium including Streptomyces WYEC 108.
[d]One hundred g of delivery medium containing *Phytophthora parasitica* was inoculated into individual hole before transplantation (450 ± 17 cfu/g of the delivery medium).
[y]Means in a column followed by the same letter are not significantly different at the P = 0.05 level.

As shown in Table VII, treatment of pepper seedlings with WYEC 108 in the absence of *P. parasitica* produced statistically significant increases in plant height, biomass, number of peppers and yield of peppers compared to control plants that did not receive WYEC 108. A comparison of horizontal rows 3 and 4 of Table IV shows that strain WYEC 108 protected peppers against the deleterious effects of *P. parasitica*. Additionally, there was a significant enhancement of the growth of plants treated with strain WYEC 108 in the absence of *P. parasitica* compared to untreated plants without *P. parasitica*.

EXAMPLE X

Protection of Plants Against Fungal Root Pathogens by Streptomyces YCED 9

The ability of Streptomyces YCED 9 to prevent a range of fungal diseases of plants was determined under both laboratory conditions and in field trials using the methods described above. The results of these tests are presented below in Table VIII. For these tests, seedlings were treated with Streptomyces YCED 9 and challenged with the fungal pathogen. Results were scored as "+" if treatment with Streptomyces YCED 9 prevented fungal infection of the seedlings based on a visual (naked eye and microscopic) inspection.

TABLE VIII

Plants Protected by Strain YCED 9

| Plant | Fungal Pathogen | Diseases | Field Test (+/−) | Lab Test (+/−) |
|---|---|---|---|---|
| Lettuce | Pythium | Damping-off | + | ND |
| Chickpea | Pythium | Seed-rot, root-rot, damping-off | + | ND |
| Green Pea | Pythium, Aphanomyces | Seed-rot, root-rot, damping-off | + | ND |
| Pepper | Phytophthora | root-rot | + | + |
| Cotton | Phytomatotrichum | root-rot | + | + |
| Turf Grass | Fusarium Rhizoctonia | root-rot brown patch | + | + |
| Onion | Phoma | Pink root | + | + |
| Potato | Fusarium Rhizoctonia | wilts, dry-rot canker | + | + |
| Tomato | Fusarium | wilts, crown-rot | + | ND[1] |

[1]Not Done

As shown in Table VIII, Streptomyces YCED 9 provides protection against a wide range of fungal diseases in a wide range of plants. Like WYEC 108, YCED 9 also colonizes young growing root tips of plants to which it is applied. To demonstrate this, onion seeds were coated with spores of YCED 9 and allowed to germinate in petri dishes on dampened filter paper. After the seeds germinated, young roots were collected at various time intervals and examined by scanning electron microscopy. Colonized roots showed the presence of *Streptomyces mycelium* on the root surfaces, while control roots (from uninoculated seeds) showed none.

Streptomyces YCED 9 is a mycoparasite of fungal root pathogens. For example, YCED 9 will colonize oospores of *Pythium ultimum* and cause them to collapse and die. Streptomyces YCED 9 will also colonize the vegetative hyphae of Phythium species and lyse the hyphae. While not wishing to be bound by speculation, it appears that mycoparasitism may be one of the major mechanisms by which strain YCED 9 acts as an antifungal agent.

EXAMPLE XI

Production of Spores of Streptomyces Bacteria in Liquid Media

Biocontrol agents must survive for extended periods of time to meet shipping needs and the timing patterns of agricultural uses. The use of spores of strain WYEC 108 or strain YCED 9 rather than vegetative cells in particular biocontrol formulations enhances the shelf-life of the biocontrol formulation because the spores retain viability under adverse conditions and over long periods of time.

Typically, spores of Streptomyces species are only produced on solid media. However, as set forth below, the following method was found suitable for producing spores in liquid culture.

Two liter Erlenmeyer flasks containing 1,200 ml medium are each inoculated with 50 ml of stock culture (produced as described in Example II) and incubated with shaking at 250 rpm at 30° C. for 12–18 days. YGM medium is preferred for WYEC 108, sporulation broth or potato dextrose medium is preferred for YCED 9. Spore production in the culture is monitored by observing with phase-contrast microscope (×1,000, and stained with methylene blue). Spores are then harvested by centrifugation at 9,000 rpm for 10 minutes.

Thereafter, the spores are resuspended in 1,600 ml of sterilized 10% medium (YGM, sporulation broth or potato dextrose broth as appropriate) and 400 ml of a sterile solution comprising 8 g $NH_4Cl$ in distilled water is added (to produce a final spore density of $1.0–1.2\times10^7$ cfu/ml). This spore mixture can be used immediately or stored at 4° C. prior to use.

Spore mixtures produced by the liquid culture method described were tested for viability after four months of storage at 4° C. One ml of spore suspension was inoculated into flasks containing 100 ml of sterilized 10% YGM liquid medium (pH6.5) and incubated with shaking at 250 rpm at 30° C. Germination of spores was observed by phase-contrast microscopy (×1,000, stained with methylene blue). Spores were completely germinated in approximately 8 days. This simple observation test showed no loss in viability after this period of storage.

The spore mixture can then be directly inoculated into a delivery medium, such as 4 kg of a pre-sterilized sterilized delivery medium consisting of sand, water and cornmeal in a 9:2:1 (w/w) ratio.

The production of spores directly in liquid culture in the described manner avoids the need for a further incubation of the mixture. The delivery medium containing spores was then stored at 4° C. until used.

The viability of a spore/delivery medium composition formulated as described (sand, water, cornmeal; 9:2:1) was tested for viability as follows. A 1.0 g sample of the delivery medium containing WYEC 108 spores was serially diluted and plated on CYD agar plates. Plates were incubated at 25° C. until colonies were formed. An average level of $10^8$ to $10^9$ cfu/g of delivery medium (dry weight) were recorded with samples stored for 30 days.

Alternatively, the spores from an agar plate of sporulation agar may be resuspended in 10–20 ml of sterile distilled water or YGM broth and mixed into 10–100 grams of delivery medium, to obtain a viable count of $10^{12}$ to $10^{14}$ cfu/g of medium. This mixture is then air-dried, mixed thoroughly and stored at 4° C. until used. This formulation is a concentrated product that can be diluted with additional delivery medium to any desired lower cfu/g final viable count.

EXAMPLE XII

Stability of Alginate Gel Formulation Containing Streptomyces Bacteria

As described above, one embodiment of this invention is the formulation of Streptomyces YCED 9 or WYEC 108 in an alginate gel. This gel mixture is particularly suitable for use in coating seeds. The following experiment was performed to confirm the viability and stability of such alginate preparations.

Mycelia of Streptomyces WYEC 108 were harvested by centrifugation at 5,000 rpm for 10 minutes from a 500 ml 3-day-old YGM liquid culture. The harvested mycelia were resuspended in 125 ml of 10% YGM and added 125 ml of sterilized 5% (w/v) sodium alginate solution to a culture density of $1.0–1.2\times10^4$ cfu/ml. Alginate pellets containing mycelia of Streptomyces WYEC 108 were formed by adding cell-alginate suspension drop by drop into sterilized 0.25M $CaCl_2$ in distilled water.

To determine the viability of the alginate pellets formed by this method, alginate pellets containing the culture were subsequently spread on a sterilized plastic petri dish (10 cm×10 cm) and dried for one hour in a laminar flow sterile air hood. The pelletized Streptomyces WYEC 108 sporulated readily following storage at 25° C. for 6 to 8 months (to an average level of $10^8$ to $10^9$ cfu/g dried alginate beads). These spores were readily germinated when they were incubated in sterilized water at 25° C. Germination of the spores were observed by phase-contrast microscopy (×1,000 magnification, stained with methylene blue).

EXAMPLE XIII

Formulation of Delivery Medium Including Streptomyces Bacteria

Having set forth above the characteristics of WYEC 108 and YCED 9 and provided methods for producing these biocontrol agents in mycelial form and as spores, and suitable delivery media, it will be apparent to one skilled in the art that the present invention can be modified in a number of ways without departing from the spirit of the invention.

Set forth below are examples of alternative embodiments of the present inventions, together with descriptions of particularly preferred embodiments.

Optimum Culture Conditions

Optimal conditions for growth of strains WYEC 108 and YCED 9 include temperatures between 20° C. and 30° C., at pHs between 5.5 and 7.5, and at fermenter agitation speeds between 200 rpm and 300 rpm. Streptomyces WYEC 108 typically achieves maximal cell mass yields of about 5.3 dry weight grams of biomass/liter in YGM liquid medium with culture conditions of 30° C., pH 6.5, and shaking at 200 rpm for 72 hr (to the end of log phase). Doubling time during logarithmic growth phase is approximately 10 hours. The 72 hr incubation time may be significantly reduced by using higher inoculum levels of log phase cells.

Alternatively, spores may be produced on solid agar media such as sporulation agar. These spores may be directly harvested by scraping into a suitable liquid medium such as 10% YGM or 10% potato dextrose medium and then directly introduced into the delivery medium. Alternatively, the spores may be mixed directly into a dry delivery medium such as peat moss/sand. This approach avoids the need for liquid growth of the culture and thereby shortens the production process, while minimizing the possibility of contamination with undesirable microorganisms.

Preferred and Alternative Delivery Media

Streptomyces WYEC 108 or Streptomyces YCED 9 may be incorporated into a delivery medium for use in horticultural and agricultural settings. Example VIII describes one formulation of the delivery medium which comprises sand-water-cornmeal in a 9-2-1 (w/w) ratio. It will be understood by one skilled in the art that the formulation of the delivery medium will be dictated by the particular application for which the biocontrol agent is intended. For example, various organic and inorganic fillers such as clay, vermiculite, wheat bran, corn cobs or chitin can be added to the delivery medium. The ratio of components of a delivery medium will be determined on the basis of texture and physical properties required. For example, properties such as moisture holding ability, light weight for easy handling and transportation, porosity to provide space for mycelial and plant root growth and spread may be important. Alternatively, vegetative mycelia or spores of Streptomyces WYEC 108 or Streptomyces YCED 9 can be added to an alginate suspension or a methyl cellulose suspension to produce alginate or methyl cellulose entrapped pellets of these bacteria. Methods of producing alginate pellets are known in the art and are described further in U.S. Pat. No. 4,668,512 to Lewis et al. Other ingredients, such as fertilizers, may also be incorporated into these pellets. These pellets may be particularly useful for broadcast spreading of YCED 9 onto turf (for example, golf courses) to prevent thatch build up and control fungal pathogens.

In a preferred embodiment, the present inventors have determined that a delivery medium comprising peat moss-sand-cornmeal in a 1:3.5:1 weight/weight ratio is particularly suitable. This ratio provides an appropriate density and water holding capacity for the use of this product in agricultural and horticultural applications. However, as stated above, other ratios of these components and of other components are also acceptable as delivery media. For example, an effective alternative delivery medium comprises peat moss (620 g)—sand (3380 g)—cornmeal (270 g)—chitin (10 g). Another delivery medium that is preferred for Streptomyces YCED 9 is sand-peat moss mixed together in a ratio of 1600 grams sand and 310 grams peat moss. The use of this delivery medium is described in Example VIII.

In one embodiment, approximately 1.6 liters of harvested culture broth (log-phase cells: e.g., about 72 hr culture) containing Streptomyces WYEC 108 mycelium grown in YGM broth or Streptomyces YCED 9 grown in potato dextrose broth as described above is supplemented with 400ml of a sterile solution of $NH_4Cl$ (containing 8 g of $NH_4Cl$ in 400 ml distilled water) and inoculated into plastic containers containing 4 kg sterilized Delivery Medium consisting of peat moss, sand, and cornmeal. The Delivery Medium is sterilized twice (3 hours at 121° C.) before inoculation with the bacteria. Inoculated containers are incubated at 30° C. for 10 to 14 days to maximize spore formation. Containers are then stored at 4° C. until used.

The use of $NH_4Cl$ in the delivery medium provides a nitrogen source for the germinating spores of the bacteria. It will be apparent to one skilled in the art that other nitrogen sources besides $NH_4Cl$ can be used for this purpose. For example, and as described herein, when spores are resuspended in bacterial growth medium (such as 10% YGM) prior to incorporation in the delivery medium, the addition of this nitrogen source is unnecessary. In preferred embodiments of the present invention, the delivery medium comprises a sufficient amount of a nitrogen source. It will be apparent to one skilled in the art that the determination of what comprises "a sufficient amount" of a nitrogen source can be made by determining the effects on germination frequency of increasing or decreasing the amount of a particular nitrogen source or the effects of changing the nitrogen source. A sufficient amount of a nitrogen source is that amount of a particular nitrogen source which facilitates germination of the spores.

In an alternative embodiment, as described in Example XI, spores of WYEC 108 or YCED 9 are produced in liquid medium and directly incorporated into the preferred delivery medium which is then stored at 4° C.

In a preferred embodiment of the present invention, Streptomyces bacteria are added to the delivery medium to a final concentration of at least $1 \times 10^5$ cfu/g. In more preferred embodiments, the final concentration of Streptomyces WYEC 108 or Streptomyces YCED 9 in the delivery medium is at least $1 \times 10^8$ cfu/g.

As discussed, one embodiment of the present invention is a composition comprising a biologically pure culture of strain WYEC 108 or YCED-9 and a delivery medium. It will be apparent to one skilled in the art that such a composition may be supplemented with additional materials or other microorganisms. For example, fertilizers or chemical pesticides may be added to the composition. In addition, other biological control agents may be combined with the composition. For example, the composition may include both Streptomyces WYEC 108 and YCED 9. Other strains of beneficial Streptomyces bacteria may also be combined with either Streptomyces WYEC 108 or Streptomyces YCED 9, provided that the additional strains are compatible with WYEC 108 or YCED 9. Compatibility can be readily determined by streaking two strains next to each other on an agar plate. If both strains grow, they are compatible. In compatibility is evidenced by the failure of one strain to grow in the presence of the other.

EXAMPLE XIV

Example of Formulation of Delivery Medium Including Streptomyces WYEC 108 or Streptomyces YCED 9

A preferred formulation of the delivery medium containing Streptomyces WYEC 108 or Streptomyces YCED 9 is produced on a large scale by the procedure set forth below. All of the procedures described are performed using standard aseptic technique (e.g., in a UV light-sterilized laminar flow chamber) to assure asepsis until the packaged bags are opened by final users. Where YGM broth is called for in the production of WYEC 108, potato dextrose broth or sporulation broth are preferred for YCED 9.

Production of Cells

1) Suspend the spores from a CYD slant of Streptomyces WYEC 108 or Streptomyces YCED 9 in 10 ml of sterile YGM broth sporulation broth or potato dextrose broth. This inoculum suspension is used to inoculate the flask cultures.

2) Inoculate six 250 ml flasks containing 100 ml YGM, PDB or SB. Use 10 ml of spore suspension per flask as inoculum. After inoculation, flasks are incubated with shaking at 200 rpm and at 30° C. for about 36 hrs.

3) Inoculate six 2.0 liter flasks each containing 1.1 liter of YGM broth (pH 6.5) PDB or SB with the mycelial inoculum prepared above (100 ml of inoculum per flask). After inoculation, flasks are incubated with shaking at 200 rpm and at 30° C. for about 24 to 48 hrs or longer (up to 4 days). This becomes the inoculum for the fermenter.

Fermentation

Approximately 7.2 liter of the stock culture prepared above is inoculated into a fermenter containing 40 liter of sterile YGM broth (pH 6.5) PDB or SB (=a 15% inoculum by volume; the approach is to inoculate with as high a density of cell suspension as practical). The fermenter is operated with agitation (200 rpm) at 30° C. for about 72 hours (to near the end of log phase).

Fermenter Harvest

1) The fermentation culture broth containing the bacterial cells (after about 72 hrs incubation) is aseptically harvested in sterile 20 liter plastic bottles.

2) Sterile $NH_4Cl$ solution is added to the harvested culture broth, which still contains the bacterial cells (Use 16 g $NH_4Cl$ or YCED9-$NH_4Cl$ dissolved in 800 ml distilled water per 3.2 liter of harvested culture broth; pre-sterilized by autoclaving). The resulting 1.2 liter volume of $NH_4Cl$-containing cell suspension is then mixed well by shaking the bottle before it is inoculated into the previously prepared delivery medium.

Preparation of the Delivery Medium

1) Each component of the Delivery Medium is measured separately and added into a large size sterilizable pan or other suitable container. The combined mixture is defined as the delivery medium. It consists of peat moss, sand, and cornmeal (540 g:2700 g: 540 g; 1:3.5:1 w/w ratio). An alternative preferred formulation is sand and peat moss in a 1600 g:310 g ratio.

2) The delivery medium is thoroughly mixed and covered with sturdy aluminum foil or cotton batting and then sterilized twice (90 minutes at a time at 121° C. with 12 hours between sterilization periods).

3) The delivery medium is cooled to room temperature after the second sterilization and before inoculation of the harvested culture broth containing strain WYEC 108 and $NH_4Cl$ solution (prepared above).

Incorporation of Streptomyces WYEC 108 or Streptomyces YCED 9 into the delivery medium to Create a Formulation of Peat Moss, Sand, Water, Cornmeal, and $NH_4Cl$ 1) About 0.5 liters of harvested culture broth containing strain WYEC 108-$NH_4Cl$ or YCED9-$NH_4Cl$ solution (prepared above) is thoroughly incorporated into each of as many as needed pre-sterilized plastic containers containing of 3.78 kg of delivery medium.

2) The inoculated containers are then incubated at 30° C. for 10 –14 days (up to 20 days incubation may be optimal) after which they can be stored at 4° C. until used (the formulation is stable for months).

Handling and Transportation

1) The completed formulation containing Streptomyces WYEC 108 or Streptomyces YCED 9 is aseptically transferred into sterile triple-layer plastic bags using a small sterilized shovel or equivalent tool, preferably in a UV-sterilized laminar flow hood.

2) The filled bags are next tied and put into 1.5 $ft^3$ moving boxes for shipping. Each box is then sealed with strong tape.

EXAMPLE XV

Incorporation of the Formulation Containing Streptomyces Bacteria into Seedling Nursery Beds The formulation containing the Streptomyces WYEC 108 or Streptomyces YCED 9 biocontrol agent and delivery medium as described in Example XIII is mixed with a plant growth medium such as nursery bedding soil or potting mix to a final Streptomyces concentration of $\geq 1.0$–$1.2 \times 10^5$ or more cfu/g-soil). The seedling procedure is as follows.

1) About 1.0 cm of peat moss is placed in the bottom of each pot (or bed) to prevent loss of soil (or potting mix) while still providing for aeration and drainage.

2) Seedling pots are then filled with the agricultural (nursery or potting mix) soil up to about 3.0 cm below from the top of the pots (or beds). The pots (beds) are then watered to saturation.

3) About 1.5 cm of the formulation containing Streptomyces WYEC 108 or Streptomyces YCED 9 and delivery medium is then added to the top of each pot (bed). If desired, the formulation can also pre-mixed with nursery bedding soil or potting soil to increase the volume and adjust the cfu/g count. However, for optimum efficacy, the cfu/g should be maintained at least $10^5$ cfu/g in the final mix.

4) Seeds are placed on the surface of the prepared seedling pots or beds and then covered with an additional 1.5 cm (approximate) of nursery bedding soil or potting soil/ mix.

5) A small amount of water is then added to wet the soil and seeds.

6) To minimize drying and to prevent crusting, the pots are typically covered with clean black plastic until seedling emergence (This may not necessary if moisture is controlled).

7) Additional water is sprayed on the top of the pots (or beds) as needed after seedling emergence.

Having provided examples of embodiments of this invention and preferred embodiments, it will be apparent to those skilled in the art that changes and modifications may be made without departing from the present invention and its broader aspects. We therefore intend the appended claims to cover all such changes and modifications falling within the true spirit and scope of the present invention.

REFERENCES

ATCC Catalogue of Bacteria and Bacteriophages, 17th Edition, 1989. American Type Culture Collection, Rockville, Md.

Filnow, A. B. and J. L. Lockwood. 1985. Evaluation of several actinomycetes and the fungus *Hypochytrium catenoides* as biocontrol agents of Phytophthora root rot of soybean. Plant Disease 69:1033–1036.

Ingram, D. M. and R. J. Cook. 1990. Pathogenicity of four Pythium species to wheat, barley, peas, and lentils. Plant Pathology 39:110–117.

Kraft, J. M. and D. W. Burke. 1971. *Pythium ultimum* as a pathogen of beans and peas in Washington. Plant Dis. Rep. 55:1056–1060.

Locci, R. 1989. "Streptomycetes and Related Genera," in *Bergey's Manual of Systematic Bacteriology*, Williams and Wilkens, Baltimore, Md. 4:2451–2492.

Lynch, J. M., R. D. Lumsden, P. T. Atkey, and M. A. Ousley. 1992. Prospects for control of Pythium damping-off of lettuce with Trichoderma, Gliocladium, and Enterobacter spp. Biol. Fertil. Soils 12:95–99.

Lynch, J. M., K. L. Wilson, M. A. Ousley, and J. M. Whipps. 1991. Response of lettuce to Trichoderma treatment. Lett. Appl. Microbiol. 12:59–61.

Miller, J. J. E. Liljeroth, G. Henken, and J. A. van Veen. 1990. Fluctuations in the fluorescent pseudomonad and actinomycete populations of rhizosphere and rhizoplane during the growth of spring wheat. Can. J. Microbiol. 36:254–258.

Pridham, T. G. and D. Gottlieb. 1948. The utilization of carbon compounds by some actinomycetales as an aid for species determination. J. Bacteriol. 56:107–114.

Reddi, G. S., and A. S. Rao. 1971. Antagonism of soil actinomycetes to some soil borne plant pathogenic fungi. Indian Phytopathol. 24: 649–657.

Stanghellini, M. E. and J. G. Hancock. 1970. A Quantitative Method for the Isolation of *Pythium ultimum* from Soil. Phytopathology. 60:551–552.

Stasz, T. E., G. E. Harman and G. A. Marx. 1980. Time and site of infection of resistant and susceptible germinating pea seeds by *Pythium ultimum*. Phytopathology. 70:730–733.

Trapero-Casas, A., W. J. Kaiser and D. M. Ingram. 1990. Control of Pythium seed rot and preemergence damping-off of chickpea in the U.S. pacific northwest and Spain. Plant Dis. 74:563–569.

Westerlund, F. V., Jr., R. N. Campbell and K. A. Kimble. 1974. Fungal root rots and wilt of chickpea in California. Phytopathology 64:432–436.

I claim:

1. A biologically pure culture of a microorganism Streptomyces YCED 9, having the identifying characteristics of ATCC 55660.

2. A composition comprising:
   a biologically pure culture of Streptomyces YCED 9, having identifying characteristics of ATCC 55660; and
   a delivery medium.

3. The composition of claim 2 wherein the delivery medium comprises alginate gel.

4. The composition of claim 2 wherein the delivery medium comprises methyl cellulose.

5. The composition of claim 2 wherein the delivery medium comprises peat moss.

6. The composition of claim 2 wherein the delivery medium comprises sand.

7. The composition of claim 2 wherein the delivery medium comprises cornmeal.

8. The composition of claim 2 wherein the delivery medium comprises a sufficient amount of a nitrogen source to support germination of spores of Streptomyces YCED 9.

9. The composition of claim 2 wherein the delivery medium comprises peat moss, sand, cornmeal and a sufficient amount of a nitrogen source to support germination of spores of Streptomyces YCED 9.

10. The composition of claim 9 wherein the nitrogen source is ammonium chloride.

11. The composition of claim 2 wherein the delivery medium comprises sand and peat moss.

12. The composition of claim 2 wherein the composition further comprises a microorganism other than Streptomyces YCED 9.

13. The composition of claim 12 wherein the microorganism other than Streptomyces YCED 9 is Streptomyces WYEC 108.

14. The composition of claim 2 wherein the biologically pure culture of Streptomyces YCED 9 comprises spores of Streptomyces YCED 9.

15. A composition comprising Streptomyces YCED 9, having identifying characteristics of ATCC 55660, and a delivery medium in a suitable container wherein the composition is useful for preventing fungal infection of a plant.

16. A method for reducing the susceptibility of a plant to fungal infection wherein the method comprises delivering a composition comprising a biologically pure culture of Streptomyces YCED 9, having identifying characteristics of ATCC 55660, to roots of the plant.

17. A method for reducing the susceptibility of plants to fungal infection wherein the method comprises the steps of:

immersing plant seeds in a composition comprising Streptomyces YCED 9, having identifying characteristics of ATCC 55660; and planting the seeds in a suitable growth medium.

18. The method of claim 17 wherein the composition further comprises alginate gel.

19. A composition comprising antimicrobial metabolites of Streptomyces YCED 9, having identifying characteristics of ATCC 55660 produced by the method of:

growing a bacterial culture comprising Streptomyces YCED 9 in a suitable growth medium; and harvesting a culture supernatant from said bacterial culture.

20. A method for reducing the susceptibility of plants to fungal infection comprising:

immersing plant seeds in a composition according to claim 19; and planting the seeds in a suitable growth medium.

21. A biologically pure culture of a Streptomyces microorganism having all of the physiological and morphological characteristics of Streptomyces YCED 9, wherein YCED 9 is deposited as ATCC 55660.

* * * * *